US005821089A

United States Patent [19]
Gruskin et al.

[11] Patent Number: 5,821,089
[45] Date of Patent: Oct. 13, 1998

[54] AMINO ACID MODIFIED POLYPEPTIDES

[76] Inventors: Elliott A. Gruskin, 23 Beech Tree Ridge, Killingworth, Conn. 06419; Douglas D. Buechter, 51 Pierson Dr., Wallingford, Conn. 06492; Guanghui Zhang, 975 Little Meadow Rd., Guilford, Conn. 06473; Kevin Connolly, 4024 La Salle Ave., Culver City, Calif. 90232

[21] Appl. No.: 655,086

[22] Filed: Jun. 3, 1996

[51] Int. Cl.⁶ .............................. C12P 21/00; C12N 5/00
[52] U.S. Cl. ...................... 435/71.1; 435/71.2; 435/348; 435/383; 435/404
[58] Field of Search .............................. 435/172.3, 348, 435/383, 404, 69.7, 71.2, 71.1, 320.1

[56] References Cited

U.S. PATENT DOCUMENTS 5,593,859   1/1997   Prockop et al. ..................... 435/69.1

FOREIGN PATENT DOCUMENTS

WO 9003438   4/1990   WIPO .

OTHER PUBLICATIONS

Klip, A. et al. J Cellular Physiol. 127(2): 244–252, May 1986.

Tan et al, "Proline Analogues Inhibit Human Skin Fibroblast Growth and Collagen Production in Culture", Journal of Investigative Dermatology, 80:261–267 (1983).

Noren et al, "A General Method For Site–Specific Incorporation of Unnatural Amino Acids Into Proteins", Science, vol. 244, pp. 182–188 (1989).

Dougherty et al, "Synthesis of a Genetically Engineered Repetitive Polypeptide Containing Periodic Selenomethioine Residues", Macromolecules, vol. 26, No. 7, pp. 1779–1781 (1993).

Uitto et al, "Procollagen Polypeptide Containing cis–4–Hydroxy–L–proline Are Overglycosylated and Secreted as Nonhelical Pro–Y–Chains", Archives of Biochemistry and Biophysics, 185:214–221 (1978).

Papas et al, "Analysis of the Amino Acid Binding to the Proline Transfer Ribonucleic Acid Synthetase of *Escherichia coli*", Journal of Biological Chemistry, 245:7:1588–1595 (1970).

Deming et al, "In Vitro Incorporation of Proline Analogs into Artificial Proteins", Poly.Mater.Sci.Engin.Proceed., vol. 71 (1994) pp. 673–674.

Ellman et al, "Site–Specific Incorporation of Novel Backbone Structures into Proteins", Science, 255:197–200 (1992).

Chung et al, "Probing the role of loop 2 in Ras function with unnatural amino acids", Proc.Natl.Acad.Sci.USA 90 (1993) pp. 10145–10149.

Randhawa et al, "Incorporation of Norleucine at Methionine Positions in Recombinant Human Macrophage Colony Stimulating Factor (M–CSF, 4–153) Expressed in *Escherichia coli*; Structural Analysis", Biochemistry, vol. 33, No. 14 (1994) pp. 4352–4362.

Koide et al, "Receptor–Binding Affinities of Human Epidermal Growth Factor Variants Having Unnatural Amino Acid Residues in Position 23", Biochemistry, vol. 33, No. 23 (1994) pp. 7470–7476.

Cornish et al, "Site–specific incorporation of biophysical probes into proteins", Proc.Natl.Acad.Sci.USA vol. 91 (1994) pp. 2910–2914.

Ellman et al, "Biosynthetic Method for Introducing Unnatural Amino Acids Site–specifically into Proteins", Methods in Enzymology, vol. 202 (1991) pp. 301–336.

Kohne et al, "Nonprotein Amino Acid Furanoymcin Unlike Isoleucine in Chemical Structure, Is Charged to Isoleucine tRNA by Isoleucyl–tRNA Synthetase and Incorporated into Protein", Journal of Biological Chemistry, vol. 265 (1990) pp. 6931–6935.

Richmond, "The Effect of Amino Acid Analogues on Growth and Protein Synthesis in Microorganisms", vol. 26 (1962) pp. 398–420.

Takeuchi et al, "Biosynthesis of Abnormal Collagens with Amino Acid Analogues" Biochimica et Biophysica Acta 175 (1969) pp. 156–164.

Uitto et al, "Incorporation of Proline Analogs into Procollagen", Archives of Biochemistry and Biophysics 181 (1977) pp. 293–299.

Rosenbloom et al, "Incorporation of 3,4–Dehydroproline into Protocollagen and Collagen", The Journal of Biological Chemistry, vol. 245 pp. 3361–3368.

Wilson et al, "Incorporation of Modified Amino Acids into Proteins In Vivo", Biochimica et Biophysica Acta, 781 (1984) pp. 205–215.

Christner et al, "Inhibition of the Assembly and Secretion of Procollagen by Incorporation of a Threonine Analogue, Hydroxynorvaline", The Journal of Biological Chemistry, vol. 250, No. 19 (1975) pp. 7623–7630.

Inouye et al., "Effects of the Stereo–Configuration of the Hydroxyl Group in 4–Hydroxyproline on the Triple–Helical Structures Formed by Homogeneous Peptides Resembling Collagen", Biochimica et Biiophysica Acta 420 (1976) pp. 133–141.

Nolan et al., "Studies on the Mechanism of Reduction of Prolyl Hydroxylase Activity by D,L–3,4 Dehydroproline", Archives of Biochemistry and Biophysics, vol. 189, No. 2 (1978) pp. 448–453.

Jimenez et al., "Decreased Thermal Stability of Collagens Containing Analogs of Proline or Lysine", Archives of Biochemistry and Biophysics 163, (1974) pp. 459–465.

(List continued on next page.)

*Primary Examiner*—David Saunders
*Assistant Examiner*—F. Pierre Vander Vegt

[57] ABSTRACT

Incorporation of certain amino acid analogs into polypeptides produced by cells which do not ordinarily provide polypeptides containing such amino acid analogs is accomplished by subjecting the cells to growth media containing such amino acid analogs. The degree of incorporation can be regulated by adjusting the concentration of amino acid analogs in the media and/or by adjusting osmolality of the media. Such incorporation allows the chemical and physical characteristics of polypeptides to be altered and studied.

21 Claims, 12 Drawing Sheets

OTHER PUBLICATIONS

Uitto et al, "Incorporation of Proline Analogues into Collagen Polypeptides", Biochimica et Biophysica Acta, 336 (1974) pp. 234–251.

Uitto et al, "Incorporation of cis–hydroxyproline into collagen by tendon cells. Failure of the intracellular collagen to assume a triple–helical conformation", Biochimica et Biophysica Acta, 278 (1972) pp. 601–605.

Jimenez et al, "Effect of Various Amion acid Analogues on Chick Tendon Procollagen Synthesis and Secretion: Selective Inhibition by S–2–Aminoethyl Cysteine", Biochemical and Biophysical Research Communications, vol. 91, No. 4 (1979) pp, 1330–1336.

Harsch et al, "Metabolism by Isolated Fibroblasts of Abnormal Collagens Containing Analogues of Proline or Lysine", FEBS Letters, vol. 26, No. 1 (1972) pp. 48–52.

Christner et al, "Effects of Incorporation of trans–4, 5–Dehydrolysine on Collagen Biosynthesis and Extrusion in Embryonic Chick Tibiae", The Journal of Biological Chemistry, vol. 246, No. 24 (1971), pp. 7551–7556.

Lane et al, "Effect of the Proline Analogue Azetidine–2–Carboxylic Acid on Collagen Synthesis In Vivo", Biochimica et Biophysica Acta 236 (1971) pp. 517–527.

Molenaar et al, "Characteristics and Osmoregulatory Roles of Uptake Systems or Proline and Glycine Betaine in *Lactococcus lactis*", Journal of Bacteriology, vol. 175, No. 17 (1993), pp. 5438–5444.

Cayley et al, "Origins of the Osmoprotective Properties of Betaine and Proline in *Escherichia coli* K–12", Journal of Bacteriology, vol. 174, No. 5 (1992) pp. 1586–1595.

Prockop et al, "The Biosynthesis of Collagen and Its Disorders", New England Journal of Medicine (1983) vol. 301, No. 1 pp. 13–22, No. 2 pp. 77–85.

Inouye et al, "Effects of the Stereo–Configuration of the Hydroxyl Group in 4–Hydroxyproline on the Triple–Helical Structures Formed By Homogeneous Peptides Resembling Collagen", Biochimica et Biophysica Acta, 420 (1976) pp. 133–141.

Venugopal et al, "Electrostatic Interactions in Collagen–like Triple–Helical Peptides", Biochemistry, vol. 33, No. 25 (1964) pp. 7948–7956.

Bella et al, "Crystal and Molecular Structure of a Collagen–Like Peptide at 1.9 A Resolution", Science, vol. 266 (1994) pp. 75–81.

Morton et al., "Integrin alpha 2 beta 1–independent activation of platelets by simple collagen like peptides: collagen tertiary (triple–helical) and quaternary (polymeric) structures are sufficient alone for alpha 2 beta 1–independent platelet reactivity." Biochemistry Journal vol. 306, (1995) pp. 337–344 Abstract only.

5'- CAGCTGTCTT ATGGCTATGA TGAGAAATCA ACCGGAGGAA TTTCCGTGCC
TGGCCCCATG GGTCCCTCTG GTCCTCGTGG TCTCCCTGGC CCCCCTGGTG
CACCTGGTCC CCAAGGCTTC CAAGGTCCCC CTGGTGAGCC TGGCGAGCCT
GGAGCTTCAG GTCCCATGGG TCCCCGAGGT CCCCCAGGTC CCCCTGGAAA
GAATGGAGAT GATGGGGAAG CTGGAAAACC TGGTCGTCCT GGTGAGCGTG
GGCCTCCTGG GCCTCAGGGT GCTCGAGGAT TGCCCGGAAC AGCTGGCCTC
CCTGGAATGA AGGGACACAG AGGTTTCAGT GGTTTGGATG GTGCCAAGGG
AGATGCTGGT CCTGCTGGTC CTAAGGGTGA GCCTGGCAGC CCTGGTGAAA
ATGGAGCTCC TGGTCAGATG GGCCCCGTG GCCTGCCTGG TGAGAGAGGT
CGCCCTGGAG CCCCTGGCCC TGCTGGTGCT CGTGGAAATG ATGGTGCTAC
TGGTGCTGCC GGGCCCCCTG GTCCCACCGG CCCCGCTGGT CCTCCTGGCT
TCCCTGGTGC TGTTGGTGCT AAGGGTGAAG CTGGTCCCCA AGGGCCCCGA
GGCTCTGAAG GTCCCCAGGG TGTGCGTGGT GAGCCTGGCC CCCCTGGCCC
TGCTGGTGCT GCTGGCCCTG CTGGAAACCC TGGTGCTGAT GGACAGCCTG
GTGCTAAAGG TGCCAATGGT GCTCCTGGTA TTGCTGGTGC TCCTGGCTTC
CCTGGTGCCC GAGGCCCCTC TGGACCCCAG GGCCCCGGCG GCCCTCCTGG
TCCCAAGGGT AACAGCGGTG AACCTGGTGC TCCTGGCAGC AAAGGAGACA
CTGGTGCTAA GGGAGAGCCT GGCCCTGTTG GTGTTCAAGG ACCCCCTGGC
CCTGCTGGAG AGGAAGGAAA GCGAGGAGCT CGAGGTGAAC CCGGACCCAC
TGGCCTGCCC GGACCCCCTG GCGAGCGTGG TGGACCTGGT AGCCGTGGTT
TCCCTGGCGC AGATGGTGTT GCTGGTCCCA AGGGTCCCGC TGGTGAACGT
GGTTCTCCTG GCCCCGCTGG CCCCAAAGGA TCTCCTGGTG AAGCTGGTCG
TCCCGGTGAA GCTGGTCTGC CTGGTGCCAA GGGTCTGACT GGAAGCCCTG
GCAGCCCTGG TCCTGATGGC AAAACTGGCC CCCCTGGTCC CGCCGGTCAA
GATGGTCGCC CCGGACCCCC AGGCCCACCT GGTGCCCGTG GTCAGGCTGG
TGTGATGGGA TTCCCTGGAC CTAAAGGTGC TGCTGGAGAG CCCGGCAAGG
CTGGAGAGCG AGGTGTTCCC GGACCCCCTG GCGCTGTCGG TCCTGCTGGC
AAAGATGGAG AGGCTGGAGC TCAGGGACCC CCTGGCCCTG CTGGTCCCGC
TGGCGAGAGA GGTGAACAAG GCCCTGCTGG CTCCCCCGGA TTCCAGGGTC
TCCCTGGTCC TGCTGGTCCT CCAGGTGAAG CAGGCAAACC TGGTGAACAG
GGTGTTCCTG GAGACCTTGG CGCCCCTGGC CCCTCTGGAG CAAGAGGCGA
GAGAGGTTTC CCTGGCGAGC GTGGTGTGCA AGGTCCCCCT GGTCCTGCTG
GACCCCGAGG GGCCAACGGT GCTCCCGGCA ACGATGGTGC TAAGGGTGAT
GCTGGTGCCC CTGGAGCTCC CGGTAGCCAG GGCGCCCCTG GCCTTCAGGG
AATGCCTGGT GAACGTGGTG CAGCTGGTCT TCCAGGGCCT AAGGGTGACA
GAGGTGATGC TGGTCCCAAA GGTGCTGATG GCTCTCCTGG CAAAGATGGC

FIG. 3A

```
GTCCGTGGTC TGACCGGCCC CATTGGTCCT CCTGGCCCTG CTGGTGCCCC
TGGTGACAAG GGTGAAAGTG GTCCCAGCGG CCCTGCTGGT CCCACTGGAG
CTCGTGGTGC CCCCGGAGAC CGTGGTGAGC CTGGTCCCCC CGGCCCTGCT
GGCTTTGCTG GCCCCCCTGG TGCTGACGGC CAACCTGGTG CTAAAGGCGA
ACCTGGTGAT GCTGGTGCCA AAGGCGATGC TGGTCCCCCT GGGCCTGCCG
GACCCGCTGG ACCCCCTGGC CCCATTGGTA ATGTTGGTGC TCCTGGAGCC
AAAGGTGCTC GCGGCAGCGC TGGTCCCCCT GGTGCTACTG GTTTCCCTGG
TGCTGCTGGC CGAGTCGGTC CTCCTGGCCC CTCTGGAAAT GCTGGACCCC
CTGGCCCTCC TGGTCCTGCT GGCAAAGAAG GCGGCAAAGG TCCCCGTGGT
GAGACTGGCC CTGCTGGACG TCCTGGTGAA GTTGGTCCCC CTGGTCCCCC
TGGCCCTGCT GGCGAGAAAG GATCCCCTGG TGCTGATGGT CCTGCTGGTG
CTCCTGGTAC TCCCGGGCCT CAAGGTATTG CTGGACAGCG TGGTGTGGTC
GGCCTGCCTG GTCAGAGAGG AGAGAGAGGC TTCCCTGGTC TTCCTGGCCC
CTCTGGTGAA CCTGGCAAAC AAGGTCCCTC TGGAGCAAGT GGTGAACGTG
GTCCCCCCGG TCCCATGGGC CCCCCTGGAT TGGCTGGACC CCCTGGTGAA
TCTGGACGTG AGGGGCTCC TGCTGCCGAA GGTTCCCCTG GACGAGACGG
TTCTCCTGGC GCCAAGGGTG ACCGTGGTGA GACCGGCCCC GCTGGACCCC
CTGGTGCTCC TGGTGCTCCT GGTGCCCCTG GCCCCGTTGG CCCTGCTGGC
AAGAGTGGTG ATCGTGGTGA GACTGGTCCT GCTGGTCCCG CCGGTCCCGT
CGGCCCCGCT GGCGCCCGTG GCCCGCCGG ACCCCAAGGC CCCCGTGGTG
ACAAGGGTGA GACAGGCGAA CAGGGCGACA GAGGCATAAA GGGTCACCGT
GGCTTCTCTG GCCTCCAGGG TCCCCCTGGC CCTCCTGGCT CTCCTGGTGA
ACAAGGTCCC TCTGGAGCCT CTGGTCCTGC TGGTCCCCGA GGTCCCCCTG
GCTCTGCTGG TGCTCCTGGC AAAGATGGAC TCAACGGTCT CCCTGGCCCC
ATTGGGCCCC CTGGTCCTCG CGGTCGCACT GGTGATGCTG GTCCTGTTGG
TCCCCCCGGC CCTCCTGGAC CTCCTGGTCC CCCTGGTCCT CCCAGCGCTG
GTTTCGACTT CAGCTTCCTC CCCCAGCCAC CTCAAGAGAA GGCTCACGAT
GGTGGCCGCT ACTACCGGGC T-3'
```

FIG. 3B

```
5'- CAGCTGTCTT ATGGCTATGA TGAGAAATCA ACCGGAGGAA TTTCCGTGCC
    TGGCCCCATG GGTCCCTCTG GTCCTCGTGG TCTCCCTGGC CCCCCTGGTG
    CACCTGGTCC CCAAGGCTTC CAAGGTCCCC CTGGTGAGCC TGGCGAGCCT
    GGAGCTTCAG GTCCCATGGG TCCCCGAGGT CCCCCAGGTC CCCCTGGAAA
    GAATGGAGAT GATGGGGAAG CTGGAAAACC TGGTCGTCCT-3'
```

FIG. 5

GGA TCC ATG GGG CTC GCT GGC CCA CCG GGC GAA CCG GGT
CCG CCA GGC CCG AAA GGT CCG CGT GGC GAT AGC GGG CTC
CCG GGC GAT TCC TAA TGG ATC C

FIG. 7

Gly-Leu-Ala-Gly-Pro-Pro-Gly-Glu-Pro-Gly-Pro-Pro-
Gly-Pro-Lys-Gly-Pro-Arg-Gly-Asp-Ser

FIG. 8

```
5'-  CAGCGGGCCA GGAAGAAGAA TAAGAACTGC CGGCGCCACT CGCTCTATGT
     GGACTTCAGC GATGTGGGCT GGAATGACTG GATTGTGGCC CCACCAGGCT
     ACCAGGCCTT CTACTGCCAT GGGGACTGCC CCTTTCCACT GGCTGACCAC
     CTCAACTCAA CCAACCATGC CATTGTGCAG ACCCTGGTCA ATTCTGTCAA
     TTCCAGTATC CCCAAAGCCT GTTGTGTGCC CACTGAACTG AGTGCCATCT
     CCATGCTGTA CCTGGATGAG TATGATAAGG TGGTACTGAA AAATTATCAG
     GAGATGGTAG TAGAGGGATG TGGGTGCCGC     -3'
```

*FIG. 10*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 3181 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:1:

```
CAGCTGTCTT   ATGGCTATGA   TGAGAAATCA   ACCGGAGGAA   TTTCCGTGCC   TGGCCCCATG        60

GGTCCCTCTG   GTCCTCGTGG   TCTCCCTGGC   CCCCCTGGTG   CACCTGGTCC   CCAAGGCTTC       120

CCAAGGCTTC   CAAGGTCCCC   CTGGTGAGCC   TGGCGAGCCT   GGAGCTTCAG   GTCCCATGGG       180

TCCCCGAGGT   CCCCCAGGTC   CCCCTGGAAA   GAATGGAGAT   GATGGGGAAG   CTGGAAAACC       240

TGGTCGTCCT   GGTGAGCGTG   GGCCTCCTGG   GCCTCAGGGT   GCTCGAGGAT   TGCCCGGAAC       300

AGCTGGCCTC   CCTGGAATGA   AGGGACACAG   AGGTTTCAGT   GGTTTGGATG   GTGCCAAGGG       360

AGATGCTGGT   CCTGCTGGTC   CTAAGGGTGA   GCCTGGCAGC   CCTGGTGAAA   ATGGAGCTCC       420

TGGTCAGATG   GGCCCCCGTG   GCCTGCCTGG   TGAGAGAGGT   CGCCCTGGAG   CCCCTGGCCC       480
```

```
TGCTGGTGCT CGTGGAAATG ATGGTGCTAC TGGTGCTGCC GGGCCCCCTG GTCCCACCGG    540
CCCCGCTGGT CCTCCTGGCT TCCCTGGTGC TGTTGGTGCT AAGGGTGAAG CTGGTCCCCA    600
AGGGCCCCGA GGCTCTGAAG GTCCCCAGGG TGTGCGTGGT GAGCCTGGCC CCCCTGGCCC    660
TGCTGGTGCT GCTGGCCCTG CTGGAAACCC TGGTGCTGAT GGACAGCCTG GTGCTAAAGG    720
TGCCAATGGT GCTCCTGGTA TTGCTGGTGC TCCTGGCTTC CCTGGTGCCC GAGGCCCCTC    780
TGGACCCCAG GGCCCCGGCG GCCCTCCTGG TCCCAAGGGT AACAGCGGTG AACCTGGTGC    840
TCCTGGCAGC AAAGGAGACA CTGGTGCTAA GGGAGAGCCT GGCCCTGTTG GTGTTCAAGG    900
ACCCCCTGGC CCTGCTGGAG AGGAAGGAAA GCGAGGAGCT CGAGGTGAAC CCGGACCCAC    960
TGGCCTGCCC GGACCCCCTG GCGAGCGTGG TGGACCTGGT AGCCGTGGTT CCCTGGCGC   1020
AGATGGTGTT GCTGGTCCCA AGGGTCCCGC TGGTGAACGT GGTTCTCCTG GCCCCGCTGG   1080
CCCCAAAGGA TCTCCTGGTG AAGCTGGTCG TCCCGGTGAA GCTGGTCTGC CTGGTGCCAA   1140
GGGTCTGACT GGAAGCCCTG GCAGCCCTGG TCCTGATGGC AAAACTGGCC CCCCTGGTCC   1200
CGCCGGTCAA GATGGTCGCC CCGGACCCCC AGGCCCACCT GGTGCCCGTG GTCAGGCTGG   1260
TGTGATGGGA TTCCCTGGAC CTAAAGGTGC TGCTGGAGAG CCCGGCAAGG CTGGAGAGCG   1320
AGGTGTTCCC GGACCCCCTG GCGCTGTCGG TCCTGCTGGC AAAGATGGAG AGGCTGGAGC   1380
TCAGGGACCC CCTGGCCCTG CTGGTCCCGC TGGCGAGAGA GGTGAACAAG GCCCTGCTGG   1440
CTCCCCCGGA TTCCAGGGTC TCCCTGGTCC TGCTGGTCCT CCAGGTGAAG CAGGCAAACC   1500
TGGTGAACAG GGTGTTCCTG GAGACCTTGG CGCCCCTGGC CCCTCTGGAG CAAGAGGCGA   1560
GAGAGGTTTC CCTGGCGAGC GTGGTGTGCA AGGTCCCCCT GGTCCTGCTG ACCCCGAGG   1620
GGCCAACGGT GCTCCCGGCA ACGATGGTGC TAAGGGTGAT GCTGGTGCCC CTGGAGCTCC   1680
CGGTAGCCAG GGCGCCCCTG GCCTTCAGGG AATGCCTGGT GAACGTGGTG CAGCTGGTCT   1740
TCCAGGGCCT AAGGGTGACA GAGGTGATGC TGGTCCCAAA GGTGCTGATG CTCTCCTGG   1800
CAAAGATGGC GTCCGTGGTC TGACCGGCCC CATTGGTCCT CCTGGCCCTG CTGGTGCCCC   1860
TGGTGACAAG GGTGAAAGTG GTCCCAGCGG CCCTGCTGGT CCCACTGGAG CTCGTGGTGC   1920
CCCCGGAGAC CGTGGTGAGC CTGGTCCCCC CGGCCCTGCT GGCTTTGCTG GCCCCCCTGG   1980
TGCTGACGGC CAACCTGGTG CTAAAGGCGA ACTGGTGAT GCTGGTGCCA AAGGCGATGC   2040
TGGTCCCCCT GGGCCTGCCG GACCCGCTGG ACCCCTGGC CCCATTGGTA ATGTTGGTGC   2100
TCCTGGAGCC AAAGGTGCTC GCGGCAGCGC TGGTCCCCCT GGTGCTACTG GTTTCCCTGG   2160
TGCTGCTGGC CGAGTCGGTC CTCCTGGCCC CTCTGGAAAT GCTGGACCCC TGGCCCTCC   2220
TGGTCCTGCT GGCAAAGAAG GCGGCAAAGG TCCCCGTGGT GAGACTGGCC CTGCTGGACG   2280
TCCTGGTGAA GTTGGTCCCC CTGGTCCCCC TGGCCCTGCT GGCGAGAAAG GATCCCCTGG   2340
TGCTGATGGT CCTGCTGGTG CTCCTGGTAC TCCCGGGCCT CAAGGTATTG CTGGACAGCG   2400
TGGTGTGGTC GGCCTGCCTG GTCAGAGAGG AGAGAGAGGC TTCCCTGGTC TTCCTGGCCC   2460
CTCTGGTGAA CCTGGCAAAC AAGGTCCCTC TGGAGCAAGT GGTGAACGTG GTCCCCCCGG   2520
TCCCATGGGC CCCCCTGGAT TGGCTGGACC CCCTGGTGAA TCTGGACGTG AGGGGCTCC   2580
TGCTGCCGAA GGTTCCCCTG GACGAGACGG TTCTCCTGGC GCCAAGGGTG ACCGTGGTGA   2640
GACCGGCCCC GCTGGACCCC CTGGTGCTCC TGGTGCTCCT GGTGCCCCTG GCCCCGTTGG   2700
CCCTGCTGGC AAGAGTGGTG ATCGTGGTGA GACTGGTCCT GCTGGTCCCG CCGGTCCCGT   2760
CGGCCCCGCT GGCGCCCGTG GCCCCGCCGG ACCCCAAGGC CCCCGTGGTG ACAAGGGTGA   2820
GACAGGCGAA CAGGGCGACA GAGGCATAAA GGGTCACCGT GGCTTCTCTG GCCTCCAGGG   2880
```

| | | | | | |
|---|---|---|---|---|---|
| TCCCCCTGGC | CCTCCTGGCT | CTCCTGGTGA | ACAAGGTCCC | TCTGGAGCCT | CTGGTCCTGC | 2940 |
| TGGTCCCCGA | GGTCCCCCTG | GCTCTGCTGG | TGCTCCTGGC | AAAGATGGAC | TCAACGGTCT | 3000 |
| CCCTGGCCCC | ATTGGGCCCC | CTGGTCCTCG | CGGTCGCACT | GGTGATGCTG | GTCCTGTTGG | 3060 |
| TCCCCCCGGC | CCTCCTGGAC | CTCCTGGTCC | CCTGGTCCT | CCCAGCGCTG | GTTTCGACTT | 3120 |
| CAGCTTCCTC | CCCCAGCCAC | CTCAAGAGAA | CGCTCACGAT | GGTGGCCGCT | ACTACCGGGC | 3180 |
| T | | | | | | 3181 |

( 2 ) INFORMATION FOR SEQ ID NO:2:

( i ) SEQUENCE CHARACTERISTICS:
        ( A ) LENGTH: 240 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:2:

| | | | | | |
|---|---|---|---|---|---|
| CAGCTGTCTT | ATGGCTATGA | TGAGAAATCA | ACCGGAGGAA | TTTCCGTGCC | TGGCCCCATG | 60 |
| GGTCCCTCTG | GTCCTCGTGG | TCTCCCTGGC | CCCCCTGGTG | CACCTGGTCC | CCAAGGCTTC | 120 |
| CAAGGTCCCC | CTGGTGAGCC | TGGCGAGCCT | GGAGCTTCAG | GTCCCATGGG | TCCCCGAGGT | 180 |
| CCCCCAGGTC | CCCCTGGAAA | GAATGGAGAT | GATGGGGAAG | CTGGAAAACC | TGGTCGTCCT | 240 |

( 2 ) INFORMATION FOR SEQ ID NO:3:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:3:

| | | | | | |
|---|---|---|---|---|---|
| GGATCCATGG | GGCTCGCTGG | CCCACCGGGC | GAACCGGGTC | CGCCAGGCCC | GAAAGGTCCG | 60 |
| CGTGGCGATA | GCGGGCTCCC | GGGCGATTCC | TAATGGATCC | | | 100 |

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:4:

| Gly | Leu | Ala | Gly | Pro | Pro | Gly | Glu | Pro | Gly | Pro | Pro | Gly | Pro | Lys | Gly |
|---|---|---|---|---|---|---|---|---|---|---|---|---|---|---|---|
| 1 | | | | 5 | | | | | 10 | | | | | 15 | |

| Pro | Arg | Gly | Asp | Ser |
|---|---|---|---|---|
| | | | | 20 |

( 2 ) INFORMATION FOR SEQ ID NO:5:

( i ) SEQUENCE CHARACTERISTICS:
        ( A ) LENGTH: 330 base pairs
        ( B ) TYPE: nucleic acid
        ( C ) STRANDEDNESS: single
        ( D ) TOPOLOGY: unknown ( i i ) MOLECULE TYPE: cDNA -continued (xi) SEQUENCE DESCRIPTION: SEQ ID NO:5:

| | | | | | | |
|---|---|---|---|---|---|---|
| CAGCGGGCCA | GGAAGAAGAA | TAAGAACTGC | CGGCGCCACT | CGCTCTATGT | GGACTTCAGC | 60 |
| GATGTGGGCT | GGAATGACTG | GATTGTGGCC | CCACCAGGCT | ACCAGGCCTT | CTACTGCCAT | 120 |
| GGGGACTGCC | CCTTTCCACT | GGCTGACCAC | CTCAACTCAA | CCAACCATGC | CATTGTGCAG | 180 |
| ACCCTGGTCA | ATTCTGTCAA | TTCCAGTATC | CCCAAAGCCT | GTTGTGTGCC | CACTGAACTG | 240 |
| AGTGCCATCT | CCATGCTGTA | CCTGGATGAG | TATGATAAGG | TGGTACTGAA | AAATTATCAG | 300 |
| GAGATGGTAG | TAGAGGGATG | TGGGTGCCGC | | | | 330 |

AMINO ACID MODIFIED POLYPEPTIDES

BACKGROUND

1. Technical Field

Engineered polypeptides having incorporated amino acids which enhance or otherwise modify properties of such polypeptides.

2. Description of Related Art

Genetic engineering allows polypeptide production to be transferred from one organism to another. In doing so, a portion of the production apparatus indigenous to an original host is transplanted into a recipient. Frequently, the original host has evolved certain unique processing pathways in association with polypeptide production which are not contained in or transferred to the recipient. For example, it is well known that mammalian cells incorporate a complex set of post-translational enzyme systems which impart unique characteristics to protein products of the systems. When a gene encoding a protein normally produced by mammalian cells is transferred into a bacterial or yeast cell, the protein may not be subjected to such post translational modification and the protein may not function as originally intended.

Normally, the process of polypeptide or protein synthesis in living cells involves transcription of DNA into RNA and translation of RNA into protein. Three forms of RNA are involved in protein synthesis: messenger RNA (mRNA) carries genetic information to ribosomes made of ribosomal RNA (rRNA) while transfer RNA (tRNA) links to free amino acids in the cell pool. Amino acid/tRNA complexes line up next to codons of mRNA, with actual recognition and binding being mediated by tRNA. Cells can contain up to twenty amino acids which are combined and incorporated in sequences of varying permutations into proteins. Each amino acid is distinguished from the other nineteen amino acids and charged to tRNA by enzymes known as aminoacyl-tRNA synthetases. As a general rule, amino acid/tRNA complexes are quite specific and normally only a molecule with an exact stereochemical configuration is acted upon by a particular aminoacyl-tRNA synthetase.

In many living cells some amino acids are taken up from the surrounding environment and some are synthesized within the cell from precursors, which in turn have been assimilated from outside the cell. In certain instances, a cell is auxotrophic, i.e., it requires a specific growth substance beyond the minimum required for normal metabolism and reproduction which it must obtain from the surrounding environment. Some auxotrophs depend upon the external environment to supply certain amino acids. This feature allows certain amino acid analogs to be incorporated into proteins produced by auxotrophs by taking advantage of relatively rare exceptions to the above rule regarding stereochemical specificity of aminoacyl-tRNA synthetases. For example, proline is such an exception, i.e., the amino acid activating enzymes responsible for the synthesis of prolyl-tRNA complex are not as specific as others. As a consequence certain proline analogs have been incorporated into bacterial, plant, and animal cell systems. See Tan et al., Proline Analogues Inhibit Human Skin Fibroblast Growth and Collagen Production in Culture, Journal of Investigative Dermatology, 80:261–267(1983).

A method of incorporating unnatural amino acids into proteins is described, e.g., in Noren et al., A General Method For Site-Specific Incorporation of Unnatural Amino Acids Into Proteins, Science, Vol. 244, pp. 182–188 (1989) wherein chemically acylated suppressor tRNA is used to insert an amino acid in response to a stop codon substituted for the codon encoding residue of interest. See also, Dougherty et al., Synthesis of a Genetically Engineered Repetitive Polypeptide Containing Periodic Selenomethionine Residues, Macromolecules, Vol. 26, No. 7, pp. 1779–1781 (1993), which describes subjecting an *E. coli* methionine auxotroph to selenomethionine containing medium and postulates on the basis of experimental data that selenomethionine may completely replace methionine in all proteins produced by the cell.

cis-Hydroxy-L-proline has been used to study its effects on collagen by incorporation into eukaryotic cells such as cultured normal skin fibroblasts (see Tan et al., supra) and tendon cells from chick embryos (see e.g., Uitto et al., Procollagen Polypeptides Containing cis-4-Hydroxy-L-proline are Overglycosylated and Secreted as Nonhelical Pro-γ-Chains, Archives of Biochemistry and Biophysics, 185:1:214–221(1978)). However, investigators found that trans-4-hydroxyproline would not link with proline specific tRNA of prokaryotic *E. coli*. See Papas et al., Analysis of the Amino Acid Binding to the Proline Transfer Ribonucleic Acid Synthetase of *Escherichia coli*, Journal of Biological Chemistry, 245:7:1588–1595(1970). Another unsuccessful attempt to incorporate trans-4-hydroxyproline into prokaryotes is described in Deming et al., In Vitro Incorporation of Proline Analogs into Artificial Proteins, Poly. Mater. Sci. Engin. Proceed., Vol. 71, p. 673–674 (1994). Deming et al. report surveying the potential for incorporation of certain proline analogs, i.e., L-azetidine-2-carboxylic acid, L-γ-thiaproline, 3,4-dehydroproline and L-trans-4-hydroxyproline into artificial proteins expressed in *E. coli* cells. Only L-azetidine-2-carboxylic acid, L-γ-thiaproline and 3,4 dehydroproline are reported as being incorporated into proteins in *E. coli* cells in vivo.

Type I collagen is the most abundant form of the fibrillar, interstitial collagens and is the main component of the extracellular matrix. Collagen monomers consist of about 1000 amino acid residues in a repeating array of Gly-X-Y triplets. Approximately 35% of the X and Y positions are occupied by proline and 4-hydroxyproline. Collagen monomers associate into triple helices which consist of one α2 and two α1 chains. The triple helices associate into fibrils which are oriented into tight bundles. The bundles of collagen fibrils are further organized to form the scaffold for extracellular matrix.

In mammalian cells, post-translational modification of collagen contributes to its ultimate chemical and physical properties and includes proteolytic digestion of pro-regions, hydroxylation of lysine and proline, and glycosylation of hydroxylated lysine. The proteolytic digestion of collagen involves the cleavage of pro regions from the N and C termini. It is known that hydroxylation of proline is essential for the mechanical properties of collagen. Collagen with low levels of 4-hydroxyproline has poor mechanical properties, as highlighted by the sequelae associated with scurvy. 4-hydroxyproline adds stability to the triple helix through hydrogen bonding and through restricting rotation about C—N bonds in the polypeptide backbone. In the absence of a stable structure, naturally occurring cellular enzymes contribute to degrading the collagen polypeptide.

The structural attributes of Type I collagen along with its generally perceived biocompatability make it a desirable surgical implant material. Collagen is purified from bovine skin or tendon and used to fashion a variety of medical devices including hemostats, implantable gels, drug delivery vehicles and bone substitutes. However, when implanted into humans bovine collagen can cause acute and delayed immune responses.

As a consequence, researchers have attempted to produce human recombinant collagen with all of its structural attributes in commercial quantities through genetic engineering. Unfortunately, production of collagen by commercial mass producers of protein such as E. coli has not been successful. A major problem is the extensive post-translational modification of collagen by enzymes not present in E. coli. Failure of E. coli cells to provide proline hydroxylation of unhydroxylated collagen proline prevents manufacture of structurally sound collagen in commercial quantities.

SUMMARY

A method of incorporating an amino acid analog into a polypeptide produced by a cell is provided which includes providing a cell selected from the group consisting of prokaryotic cell and eukaryotic cell, providing growth media containing at least one amino acid analog selected from the group consisting of trans-4-hydroxyproline, 3-hydroxyproline, cis-4-fluoro-L-proline and combinations thereof and contacting the cell with the growth media wherein the at least one amino acid analog is assimilated into the cell and incorporated into at least one polypeptide.

Also provided is a method of substituting an amino acid analog of an amino acid in a polypeptide produced by a cell selected from the group consisting of prokaryotic cell and eukaryotic cell, which includes providing a cell selected from the group consisting of prokaryotic cell and eukaryotic cell, providing growth media containing at least one amino acid analog selected from the group consisting of trans-4-hydroxyproline, 3-hydroxyproline, cis-4-fluoro-L-proline and combinations thereof and contacting the cell with the growth media wherein the at least one amino acid analog is assimilated into the cell and incorporated as a substitution for at least one naturally occurring amino acid in at least one polypeptide.

A method of controlling the amount of an amino acid analog incorporated into a polypeptide is also provided which includes providing at least a first cell selected from the group consisting of prokaryotic cell and eukaryotic cell, providing a first growth media containing a first predetermined amount of at least one amino acid analog selected from the group consisting of trans-4-hydroxyproline, 3-hydroxyproline, cis-4-fluoro-L-proline and combinations thereof and contacting the first cell with the first growth media wherein a first amount of amino acid analog is assimilated into the first cell and incorporated into at least one polypeptide. At least a second cell selected from the group consisting of prokaryotic cell and eukaryotic cell, is also provided along with a second growth media containing a second predetermined amount of an amino acid analog selected from the group consisting of trans-4-hydroxyproline, 3-hydroxyproline, cis-4-fluoro-L-proline and combinations thereof and the at least second cell is contacted with the second growth media wherein a second amount of amino acid analog is assimilated into the second cell and incorporated into at least one polypeptide.

Also provided is a method of increasing stability of a recombinant polypeptide produced by a cell which includes providing a cell selected from the group consisting of prokaryotic cell and eukaryotic cell, and providing growth media containing an amino acid analog selected from the group consisting of trans-4-hydroxyproline, 3-hydroxyproline, cis-4-fluoro-L-proline and combinations thereof and contacting the cell with the growth media wherein the amino acid analog is assimilated into the cell and incorporated into a recombinant polypeptide, thereby stabilizing the polypeptide.

A method of increasing uptake of an amino acid analog into a cell and causing formation of an amino acid analog/tRNA complex is also provided which includes providing a cell selected from the group consisting of prokaryotic cell and eukaryotic cell, providing hypertonic growth media containing amino acid analog selected from the group consisting of trans-4-hydroxyproline, 3-hydroxyproline, cis-4-fluoro-L-proline and combinations thereof and contacting the cell with the hypertonic growth media wherein the amino acid analog is assimilated into the cell and incorporated into an amino acid analog/tRNA complex. In any of the other above methods, a hypertonic growth media can optionally be incorporated to increase uptake of an amino acid analog into a cell.

A composition is provided which includes a cell selected from the group consisting of prokaryotic cell and eukaryotic cell, and hypertonic media including an amino acid analog selected from the group consisting of trans-4-hydroxyproline, 3-hydroxyproline, cis-4-fluoro-L-proline and combinations thereof.

BRIEF DESCRIPTION OF THE DRAWINGS

FIGS. 3A and 3B depict a DNA sequence encoding human Type 1 ($\alpha$1) collagen (Seq. ID No. 1).

FIG. 5 depicts a DNA sequence encoding a fragment of human Type 1 ($\alpha$1) collagen (Seq. ID No. 2).

FIG. 7 depicts a DNA sequence encoding a collagen-like peptide (Seq. ID No. 3).

FIG. 8 depicts an amino acid sequence of a collagen-like peptide (Seq. ID No. 4).

FIG. 10 depicts a DNA sequence encoding mature bone morphogenic protein (Seq. ID No. 5).

DETAILED DESCRIPTION OF PREFERRED EMBODIMENTS

Prokaryotic cells and eukaryotic cells can unexpectedly be made to assimilate and incorporate trans-4-hydroxyproline into proteins contrary to both Papes et al. and Deming et al., supra. Such assimilation and incorporation is especially useful when the structure and function of a polypeptide depends on post translational hydroxylation of proline not provided by the native protein production system of a recombinant host. Thus, prokaryotic bacteria such as E. coli and eukaryotic cells such as Saccharomyces cerevisiae, Saccharomyces carlsbergensis and Schizosaccharomyces pombe that ordinarily do not hydroxylate proline and additional eukaryotes such as insect cells including lepidopteran cell lines including Spodoptera frugiperda, Trichoplasia ni, Heliothis virescens, Bombyx mori infected with a baculovirus; CHO cells, COS cells and NIH 3T3 cells which fail to adequately produce certain polypeptides whose structure and function depend on such hydroxylation can be made to produce polypeptides having hydroxylated prolines. Incorporation includes adding trans-4-hydroxyproline to a polypeptide, for example, by first changing an amino acid to proline, creating a new proline position that can in turn be substituted with trans-4-hydroxyproline or substituting a naturally occurring proline in a polypeptide with trans-4-hydroxyproline as well.

The process of producing recombinant polypeptides in mass producing organisms is well known. Replicable expression vectors such as plasmids, viruses, cosmids and artificial chromosomes are commonly used to transport genes encoding desired proteins from one host to another. It is contemplated that any known method of cloning a gene, ligating the gene into an expression vector and transforming a host cell with such expression vector can be used in furtherance of the present disclosure.

Not only is incorporation of trans-4-hydroxyproline into polypeptides which depend upon trans-4-hydroxyproline for chemical and physical properties useful in production systems which do not have the appropriate systems for converting proline to trans-4-hydroxyproline, but useful as well in studying the structure and function of polypeptides which do not normally contain trans-4-hydroxyproline. It is contemplated that the following amino acid analogs may also be incorporated in accordance with the present disclosure: trans-4 hydroxyproline, 3-hydroxyproline, cis-4-fluoro-L-proline and combinations thereof (hereinafter referred to as the "amino acid analogs"). Use of prokaryotes and eukaryotes is desirable since they allow relatively inexpensive mass production of such polypeptides. It is contemplated that the amino acid analogs can be incorporated into any desired polypeptide. In a preferred embodiment the prokaryotic cells and eukaryotic cells are starved for proline by decreasing or eliminating the amount of proline in growth media prior to addition of an amino acid analog herein.

Figure 1:
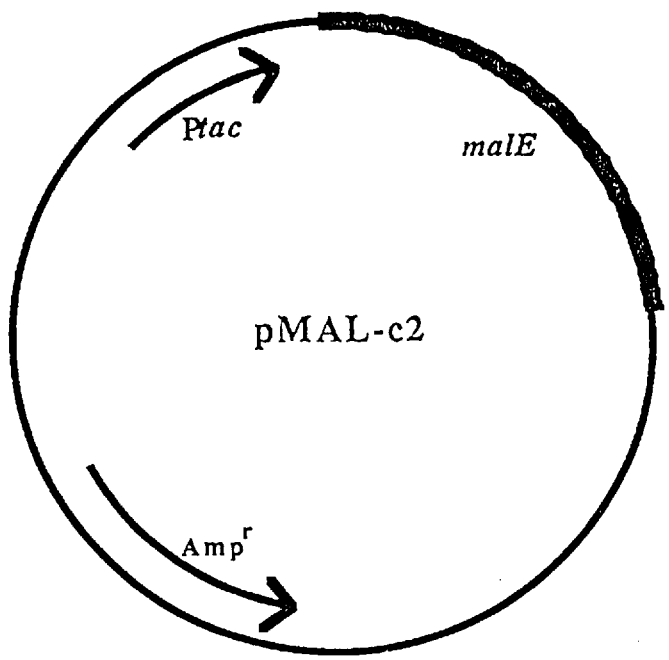
FIG. 1 is a plasmid map illustrating pMAL-c2.
Figure 2:
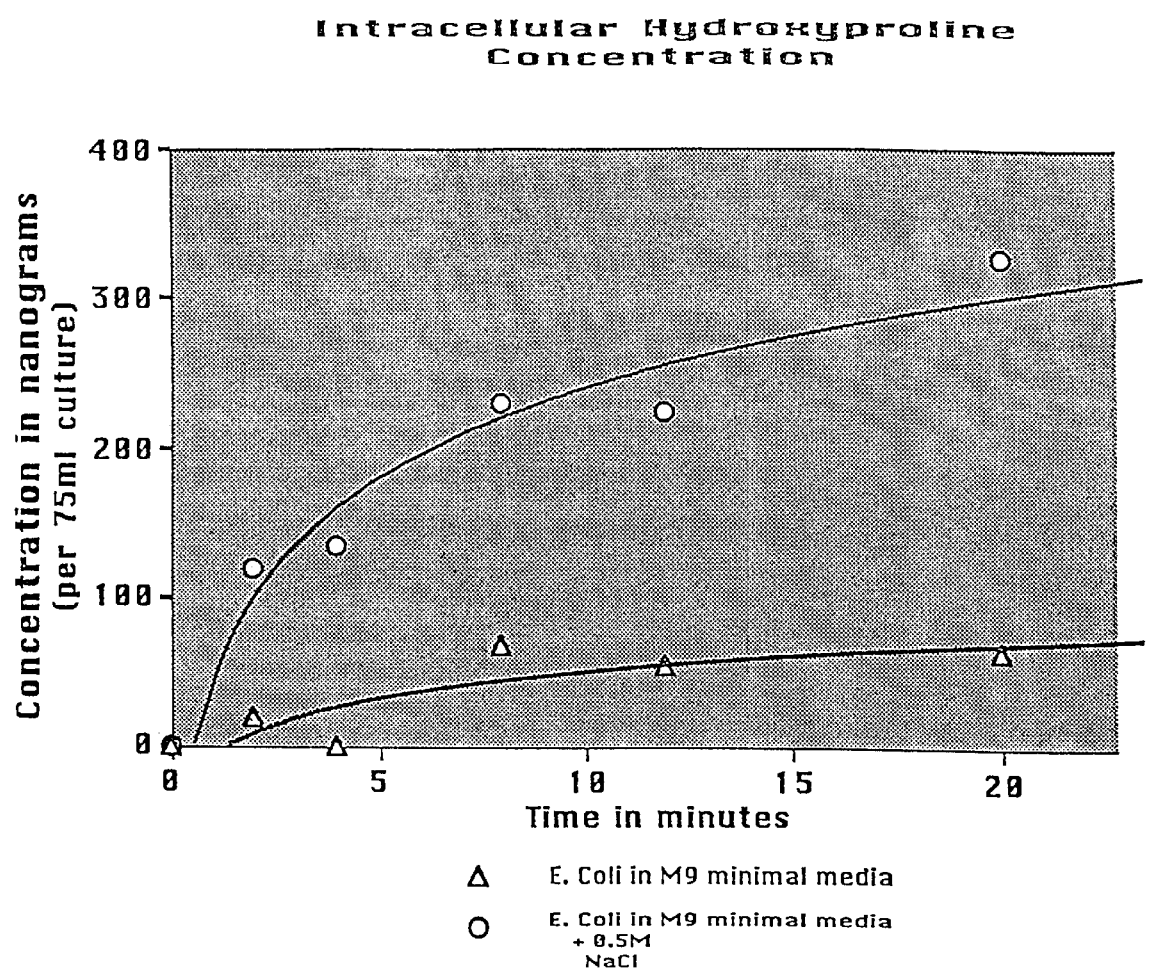
FIG. 2 is a graphical representation of the concentration of intracellular hydroxyproline based upon concentration of trans-4-hydroxyproline in growth culture over time.

Expression vectors containing the gene for maltose binding protein (MBP), e.g., see FIG. 1 illustrating plasmid pMAL-c2, commercially available from New England Bio-Labs, are transformed into prokaryotes such as *E. coli* proline auxotrophs or eukaryotes such as *S. cerevisiae* auxotrophs which depend upon externally supplied proline for protein synthesis and anabolism. Other preferred expression vectors for use in prokaryotes are commercially available plasmids which include pKK-223 (Pharmacia), pTRC (Invitrogen), pGEX (Pharmacia), pET (Novagen) and pQE (Quiagen). Substitution of the amino acid analogs for proline in protein synthesis occurs since prolyl tRNA synthetase is sufficiently promiscuous to allow misacylation of proline tRNA with any one of the amino acid analogs. A sufficient quantity, i.e., typically ranging from about 0.001M to about 0.1M, but more preferably from about 0.005M to about 0.5M of the amino acid analog(s) is added to the growth medium for the transformed cells to compete with proline in cellular uptake. After sufficient time, generally from about 30 minutes to about 24 hours or more, the amino acid analog(s) is assimilated by the cell and incorporated into protein synthetic pathways. As can be seen from FIG. 2, intracellular concentration of trans-4-hydroxyproline increases by increasing the concentration of trans-4-hydroxyproline in the growth media. In a preferred embodiment the prokaryotic cells and/or eukaryotic cells are starved for proline by decreasing or eliminating the amount of proline in growth media prior to addition of an amino acid analog herein.

Figure 4:
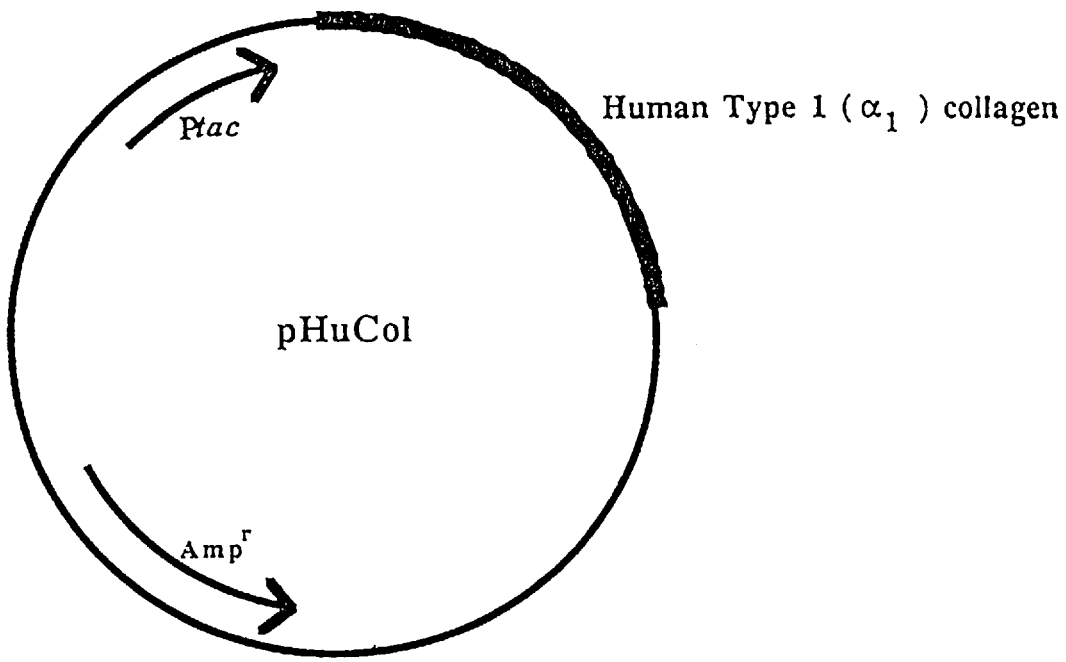
FIG. 4 is a plasmid map illustrating pHuCol.

Expression vectors containing the gene for human Type I (α1) collagen (DNA sequence illustrated in FIGS. 3A and 3B (Seq. ID No. 1); plasmid map illustrated in FIG. 4) are transformed into prokaryotic or eukaryotic proline auxotrophs which depend upon externally supplied proline for protein synthesis and anabolism. As above, substitution of the amino acid analog(s) occurs since prolyl tRNA synthetase is sufficiently promiscuous to allow misacylation of proline tRNA with the amino acid analog(s). The quantity of amino acid analog(s) in media given above is again applicable.

Figure 6:
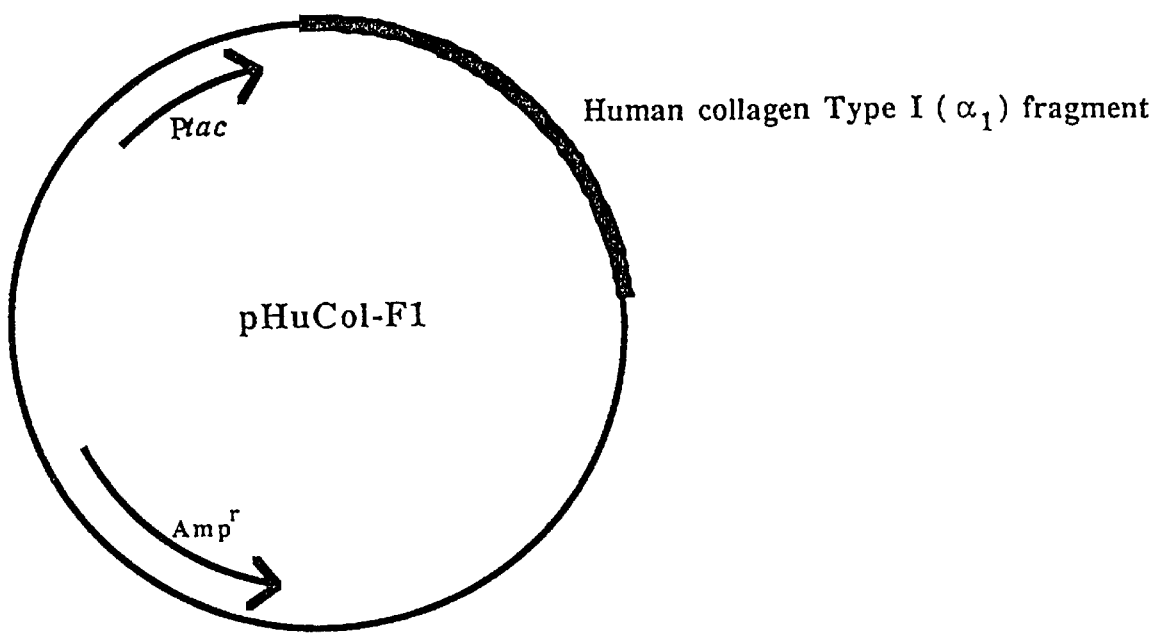
FIG. 6 is a plasmid map illustrating pHuCol-Fl.
Figure 9:
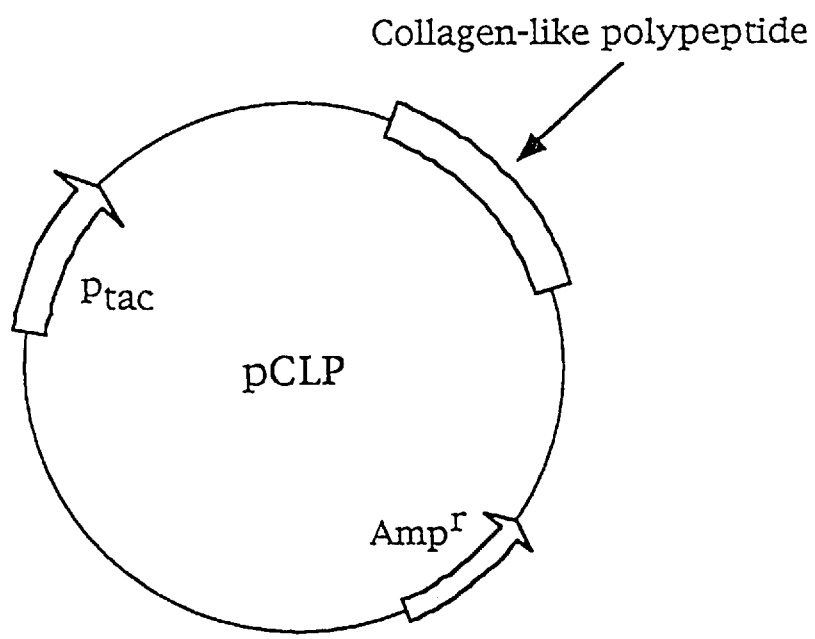
FIG. 9 is a plasmid map illustrating pCLP.

Expression vectors containing DNA encoding fragments of human Type 1 (α1) collagen (e.g., DNA sequence illustrated in FIG. 5 (Seq. ID No. 2) and plasmid map illustrated in FIG. 6) are transformed into prokaryotic or eukaryotic auxotrophs as above. Likewise, expression vectors containing DNA encoding collagen-like polypeptide (e.g., DNA sequence illustrated in FIG. 7 (Seq. ID No. 3), amino acid sequence illustration in FIG. 8 (Seq. ID No. 4) and plasmid map illustrated in FIG. 9) can be used to transform prokaryotic or eukaryotic auxotrophs as above. Collagen-like peptides are those which contain at least partial homology with collagen and exhibit similar chemical and physical characteristics to collagen. Thus, collagen-like peptides consist, e.g., of repeating arrays of Gly-X-Y triplets in which about 35% of the X and Y positions are occupied by proline and 4-hydroxyproline. Certain preferred collagen fragments and collagen-like peptides in accordance herewith are capable of assembling into an extracellular matrix. In both collagen fragments and collagen-like peptides as described above, substitution with amino acid analog(s) occurs since prolyl tRNA synthetase is sufficiently promiscuous to allow misacyclation of proline tRNA with one or more of the amino acid analog(s). The quantity of amino acid analog(s) given above is again applicable.

Figure 11:
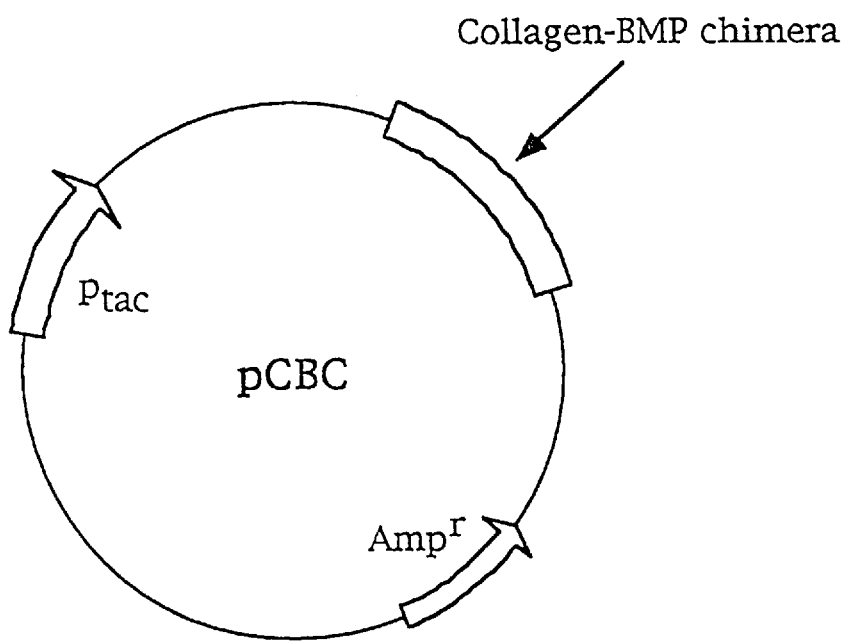
FIG. 11 is a plasmid map illustrating pCBC.

It is contemplated that any polypeptide having a collagen, collagen fragment or collagen-like peptide domain can be made to incorporate amino acid analog(s) in accordance with the disclosure herein. Such polypeptides include collagen, a collagen fragment or collagen-like peptide domain and a domain having a region incorporating one or more physiologically active substances such as glycoproteins, proteins, peptides and proteoglycans. Physiologically active substances exert control over or modify existing physiologic functions in living things. Physiologically active substances include hormones, growth factors, enzymes, ligands and receptors. Many active domains of physiologically active substances have been defined and isolated. It is contemplated that polypeptides having a collagen, collagen fragment or collagen-like peptide domain can also have a domain incorporating one or more physiologically active domains which are active fragments of such physiologically active substances. Thus, chimeric proteins are made to incorporate amino acid analog(s) by transforming a prokaryotic proline auxotroph or a eukaryotic proline auxotroph with an appropriate expression vector and contacting the transformed auxotroph with growth media containing at least one of the amino acid analogs. For example, a chimeric collagen/bone morphogenic protein (BMP) construct or various chimeric collagen/growth factor constructs are useful in accordance herein. Such growth factors are well-known and include insulin-like growth factor, transforming growth factor, platelet derived growth factor and the like. FIG. 10 illustrates DNA of BMP (Seq. ID No. 5) which can be fused to the 3' terminus of DNA encoding collagen, DNA encoding a collagen fragment or DNA encoding a collagen-like peptide. FIG. 11 illustrates a map of plasmid pCBC containing a collagen/BMP construct. In a preferred embodiment, proteins having a collagen, collagen fragment or collagen-like peptide domain assemble to form an extracellular matrix which can be used as a surgical implant.

Figure 12:
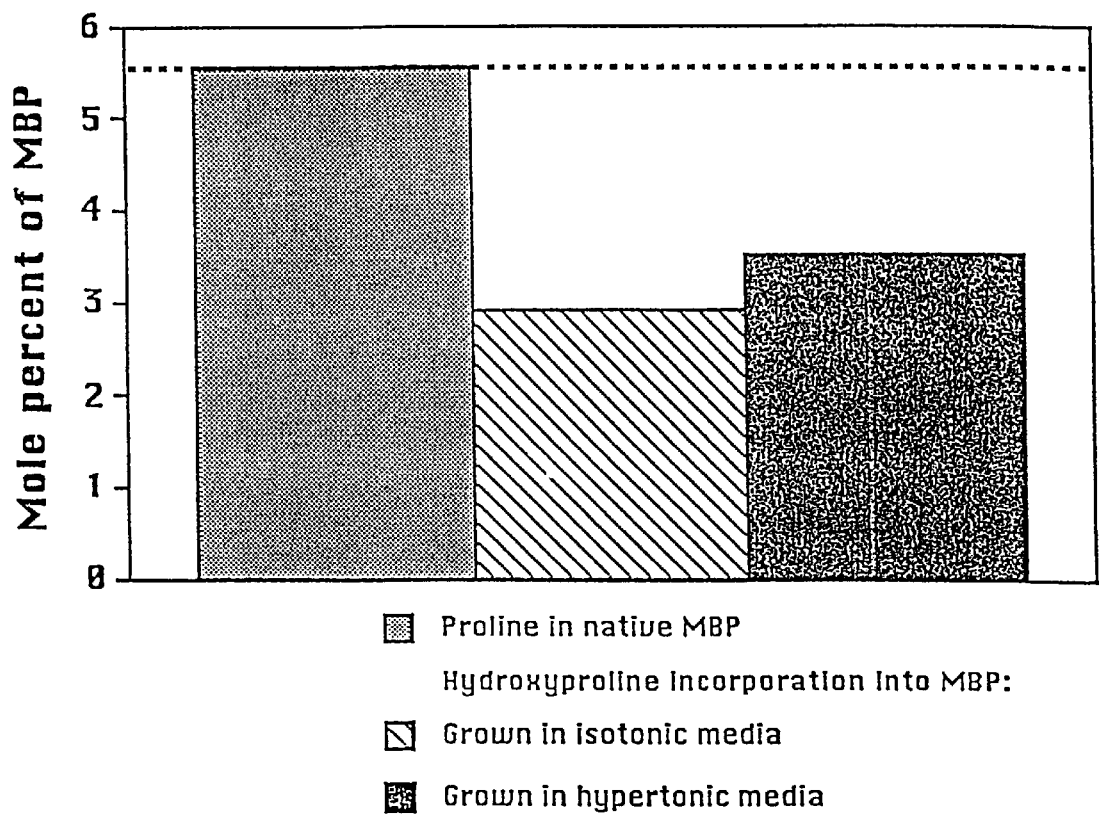
FIG. 12 is a graphical representation of the percent incorporation of proline and trans-4-hydroxyproline into maltose binding protein under various conditions.

In another aspect, the amount of amino acid analog(s) transport into a target cell can be regulated by controlling the tonicity of the growth media. A hypertonic growth media increases uptake of trans-4-hydroxyproline into *E. coli* as illustrated in FIG. 12. All known methods of increasing osmolality of growth media are appropriate for use herein including addition of salts such as sodium chloride, KCl, $MgCl_2$ and the like, and sugars such as sucrose, glucose, maltose, etc. and polymers such as polyethylene glycol (PEG), dextran, cellulose, etc. and amino acids such as glycine. Increasing the osmolality of growth media results in greater intracellular concentration of amino acid analog(s) and a higher degree of complexation of amino acid analog(s) to tRNA. As a consequence, proteins produced by the cell achieve a higher degree of incorporation of amino acid analogs. FIG. 12 illustrates percentage of incorporation of proline and hydroxyproline into MBP under isotonic and hypertonic media conditions in comparison to proline in native MBP. Thus, manipulating osmolality, in addition to adjusting concentration of amino acid analog(s) in growth media allows a dual-faceted approach to regulating their uptake into prokaryotic cells and eukaryotic cells as described above and consequent incorporation into target polypeptides.

Any growth media can be used herein including commercially available growth media such as M9 minimal medium (available from Gibco Life Technologies, Inc.), LB medium, NZCYM medium, terrific broth, SOB medium and others that are well known in the art.

Collagen from different tissues can contain different amounts of trans-4-hydroxyproline. For example, tissues that require greater strength such as bone contain a higher number of trans-4-hydroxyproline residues than collagen in tissues requiring less strength, e.g., skin. The present system provides a method of adjusting the amount of trans-4-hydroxyproline in collagen, collagen fragments, collagen-like peptides, and chimeric polypeptides having a collagen domain, collagen fragment domain or collagen-like peptide domain fused to a physiologically active domain, since by increasing or decreasing the concentration of trans-4-hydroxyproline in growth media, the amount of trans-4-hydroxyproline incorporated into such polypeptides is increased or decreased accordingly. The collagen, collagen fragments, collagen-like peptides and above-chimeric peptides can be expressed with predetermined levels of trans-4-hydroxyproline. In this manner physical characteristics of an extracellular matrix can be adjusted based upon requirements of end use.

Human collagen, collagen fragments, collagen-like peptides and the above chimeric polypeptides produced by recombinant processes have distinct advantages over collagen and its derivatives obtained from non-human animals. Since the human gene is used, the collagen will not act as a xenograft in the context of a medical implant. Moreover, unlike naturally occurring collagen, the extent of proline hydroxylation can be predetermined. This unprecedented degree of control permits detailed investigation of the contribution of trans-4-hydroxyproline to triple helix stabilization, fibril formation and biological activity. In addition, design of medical implants based upon the desired strength of collagen fibrils is enabled.

The following examples are included for purposes of illustration and are not to be construed as limitations herein.

EXAMPLE 1

Trans-membrane Transport

A 5 mL culture of *E. coli* strain DH5α (supE44 ΔlacU169 (φ80lacZ ΔM15) hsdR17 recA1 endA1 gyrA96 thi-1 relA1) containing a plasmid conferring resistance to ampicillin (pMAL-c2, FIG. 1) was grown in Luria Broth to confluency (~16 hours from inoculation). These cells were used to inoculate a 1 L shaker flask containing 500 mL of M9 minimal medium (M9 salts, 2% glucose, 0.01 mg/mL thiamine, 100 μg/mL ampicillin supplemented with all amino acids at 20 μg/mL) which was grown to an $AU_{600}$ of 1.0 (18–20 hours). The culture was divided in half and the cells harvested by centrifugation. The cells from one culture, were resuspended in 250 mL M9 media and those from the other in 250 mL of M9 media containing 0.5M NaCl. The cultures were equilibrated in an air shaker for 20 minutes at 37° C. (225 rpm) and divided into ten 25 mL aliquots. The cultures were returned to the shaker and 125 μL of 1M hydroxyproline in distilled $H_2O$ was added to each tube. At 2, 4, 8, 12, and 20 minutes, 4 culture tubes (2 isotonic, 2 hypertonic) were vacuum filtered onto 1 μm polycarbonate filters that were immediately placed into 2 mL microfuge tubes containing 1.2 mL of 0.2M NaOH/2% SDS in distilled $H_2O$. After overnight lysis, the filters were carefully removed from the tubes, and the supernatant buffer was assayed for hydroxyproline according to the method of Grant, Journal of Clinical Pathology, 17:685 (1964). The intracellular concentration of trans-4-hydroxyproline versus time is illustrated graphically in FIG. 2.

EXAMPLE 2

Effects of Salt Concentration on Transmembrane Transport

To determine the effects of salt concentration on transmembrane transport, an approach similar to Example 1 was taken. A 5 mL culture of *E. coli* strain DH5α (supE44 ΔlacU169 (φ80lacZ ΔM15) hsdR17 recA1 endA1 gyrA96 thi-1 relA1) containing a plasmid conferring resistance to ampicillin (pMAL-c2, FIG. 1) was grown in Luria Broth to confluency (~16 hours from inoculation). These cells were used to inoculate a 1 L shaker flask containing 500 mL of M9 minimal medium (M9 salts, 2% glucose, 0.01 mg/mL thiamine, 100 μg/mL ampicillin supplemented with all amino acids at 20 μg/mL) that was then grown to an $AU_{600}$ of 0.6. The culture was divided into three equal parts, the cells in each collected by centrifugation and resuspended in 150 mL M9 media, 150 mL M9 media containing 0.5M NaCl, and 150 mL M9 media containing 1.0M NaCl, respectively. The cultures were equilibrated for 20 minutes on a shaker at 37° C. (225 rpm) and then divided into six 25 mL aliquots. The cultures were returned to the shaker and 125 μL of 1M hydroxyproline in distilled $H_2O$ was added to each tube. At 5 and 15 minutes, 9 culture tubes (3 isotonic, 3×0.5M NaCl, and 3×1.0M NaCl) were vacuum filtered onto 1 μm polycarbonate filters that were immediately placed into 2 mL microfuge tubes containing 1.2 mL of 0.2M NaOH/2% SDS in distilled $H_2O$. After overnight lysis, the filters were removed from the tubes and the supernatant buffer assayed for hydroxyproline according to the method of Grant, supra.

EXAMPLE 3

Determination of Proline Starvation Conditions in *E. coli*

Proline auxotrophic *E. coli* strain NM519 (pro) including plasmid pMAL-c which confers ampicillin resistance was grown in M9 minimal medium (M9 salts, 2% glucose, 0.01 mg/mL thiamine, 100 microgram/mL ampicillin supplemented with all amino acids at 20 µg/mL except proline which was supplemented at 12.5 mg/L) to a constant $AU_{600}$ of 0.53 AU (17 hours post-inoculation). Hydroxyproline was added to 0.08M and hydroxyproline-dependent growth was demonstrated by the increase in the $OD_{600}$ to 0.61 AU over a one hour period.

EXAMPLE 4

Hydroxyproline Incorporation into Protein in *E. coli* under Proline Starvation Conditions Plasmid pMAL-c2 (commercially available from New England Biolabs) containing DNA encoding for maltose-binding protein (MBP) was used to transform proline auxotrophic *E. coli* strain NM519 (pro⁻). Two 1 L cultures of transformed NM519 (pro⁻) in M9 minimal medium (M9 salts, 2% glucose, 0.01 mg/mL thiamine, 100 µg/mL ampicillin supplemented with all amino acids at 20 µg/mL except proline which was supplemented at 12.5 mg/L) were grown to an $AU_{600}$ Of 0.53 (~17 hours post-inoculation). The cells were harvested by centrifugation, the media in one culture was replaced with an equal volume of M9 media containing 0.08M hydroxyproline and the media in the second culture was replaced with an equal volume of M9 media containing 0.08M hydroxyproline and 0.5M NaCl. After a one hour equilibration, the cultures were induced with 1 mM isopropyl-β-D-thiogalactopyranoside. After growing for an additional 3.25 hours, cells were harvested by centrifugation, resuspended in 10 mL of 10 mM Tris-HCl (pH 8), 1 mM EDTA, 100 mM NaCl (TEN buffer), and lysed by freezing and sonication. MBP was purified by passing the lysates over 4 mL amylose resin spin columns, washing the columns with 10 mL of TEN buffer, followed by elution of bound MBP with 2 mL of TEN buffer containing 10 mM maltose. Eluted samples were sealed in ampules under nitrogen with an equal volume of concentrated HCl (11.7M) and hydrolysed for 12 hours at 120° C. After clarification with activated charcoal, hydroxyproline content in the samples was determined by HPLC and the method of Grant, supra. The percent incorporation of trans-4-hydroxyproline compared to proline into MBP is shown graphically in FIG. 12.

EXAMPLE 5

Hydroxyproline Incorporation into Protein in *S. cerevisiae* via Integrating Vectors under Proline Starvation Conditions The procedure described in Example 4 above is performed in yeast using an integrating vector which disrupts the proline biosynthetic pathway. A gene encoding human Type 1 ($\alpha_1$) collagen is inserted into a unique shuttle vector behind the inducible GAL10 promoter. This promoter/gene cassette is flanked by a 5' and 3' terminal sequence derived from a *S. cerevisiae* proline synthetase gene. The plasmid is linearized by restriction digestion in both the 5' and 3' terminal regions and used to transform a proline-prototrophic *S. cerevisiae* strain. The transformation mixture is plated onto selectable media and transformants are selected. By homologous recombination and gene disruption, the construct simultaneously forms a stable integration and converts the *S. cerevisiae* strain into a proline auxotroph. A single transformant is selected and grown at 30° C. in YPD media to an $OD_{600}$ of 2 AU. The culture is centrifuged and the cells resuspended in yeast dropout media supplemented with all amino acids except proline and grown to a constant $OD_{600}$ indicating proline starvation conditions. 0.08M L-hydroxyproline and 2% (w/v) galactose is then added. Cultures are grown for an additional 6–48 hours. Cells are harvested by centrifugation (5000 rpm, 10 minutes) and lysed by mechanical disruption. Hydroxyproline-containing human Type 1 ($\alpha_1$) collagen is purified by ammonium sulfate fractionation and column chromatography.

EXAMPLE 6

Hydroxyproline Incorporation into Protein in *S. cerevisiae* via Non-Integrating Vectors under Proline Starvation Conditions The procedure described above in Example 4 is performed in a yeast proline auxotroph using a non-integrating vector. A gene encoding human Type 1 ($\alpha_1$) collagen is inserted behind the inducible GAL10 promoter in the YEp24 shuttle vector that contains the selectable Ura⁺ marker. The resulting plasmid is transformed into proline auxotrophic *S. cerevisiae* by spheroplast transformation. The transformation mixture is plated on selectable media and transformants are selected. A single transformant is grown at 30° C. in YPD media to an $OD_{600}$ of 2 AU. The culture is centrifuged and the cells resuspended in yeast dropout media supplemented with all amino acids except proline and grown to a constant $OD_{600}$ indicating proline starvation conditions. 0.08M L-hydroxyproline and 2% (w/v) galactose is then added. Cultures are grown for an additional 6–48 hours. Cells are harvested by centrifugation (5000 rpm, 10 minutes) and lysed by mechanical disruption. Hydroxyproline-containing human Type 1 ($\alpha_1$) collagen is purified by ammonium sulfate fractionation and column chromatography.

EXAMPLE 7

Hydroxyproline Incorporation into Protein in a Baculovirus Expression System

A gene encoding human Type 1 ($\alpha_1$) collagen is inserted into the pBacPAK8 baculovirus expression vector behind the AcMNPV polyhedron promoter. This construct is co-transfected into SF9 cells along with linearized AcMNPV DNA by standard calcium phosphate co-precipitation. Transfectants are cultured for 4 days at 27° C. in TNM-FH media supplemented with 10% FBS. The media is harvested and recombinant virus particles are isolated by a plaque assay. Recombinant virus is used to infect 1 liter of SF9 cells growing in Grace's media minus proline supplemented with 10% FBS and 0.08M hydroxyproline. After growth at 27° C. for 2–10 days, cells are harvested by centrifugation and lysed by mechanical disruption. Hydroxyproline-containing human Type 1 ($\alpha_1$) collagen is purified by ammonium sulfate fractionation and column chromatography.

EXAMPLE 8

Hydroxyproline Incorporation into Human Collagen Protein in *Escherichia coli* Under Proline Starvation Conditions A plasmid (pHuCol, FIG. 2) encoding the gene sequence of human Type I ($\alpha_1$) collagen (FIGS. 3A and 3B (Seq. ID No. 1 placed behind the isopropyl-β-D-thiogalactopyranoside (IPTG)-inducible tac promotor and also encoding β-lactamase is transformed into *Escherichia coli* proline auxotrophic strain NM519 (pro⁻) by standard heat shock transformation. Transformation cultures are plated on Luria Broth (LB) containing 100 μg/ml ampicillin and after overnight growth a single ampicillin-resistant colony is used to inoculate 5 ml of LB containing 100 μg/ml ampicillin. After growth for 10–16 hours with shaking (225 rpm) at 37° C., this culture is used to inoculate 1 L of M9 minimal medium (M9 salts, 2% glucose, 0.01 mg/mL thiamine, 100 μg/ml ampicillin, supplemented with all amino acids at 20 μg/mL except proline which is supplemented at 12.5 mg/L) in a 1.5 L shaker flask. After growth at 37° C., 225 rpm, for 15–20 hours post-inoculation, the optical density at 600 nm is constant at approximately 0.5 OD/ml. The cells are harvested by centrifugation (5000 rpm, 5 minutes), the media decanted, and the cells resuspended in 1 L of M9 minimal media containing 100 μg/ml ampicillin, 0.08M L-hydroxyproline, and 0.5M NaCl. Following growth for 1 hour at 37° C., 225 rpm, IPTG is added to 1 mM and the cultures allowed to grow for an additional 5–15 hours. Cells are harvested by centrifugation (5000 rpm, 10 minutes) and lysed by mechanical disruption. Hydroxyproline-containing collagen is purified by ammonium sulfate fractionation and column chromatography.

EXAMPLE 9

Hydroxyproline Incorporation into Fragments of Human Collagen Protein in *Escherichia coli* under Proline Starvation Conditions A plasmid (pHuCol-Fl, FIG. 6) encoding the gene sequence of the first 80 amino acids of human Type 1 ($\alpha_1$) collagen (FIG. 5 (Seq. ID No. 2) placed behind the isopropyl-β-D-thiogalactopyranoside (IPTG)-inducible tac promotor and also encoding β-lactamase is transformed into *Escherichia coli* proline auxotrophic strain NM519 (pro⁻) by standard heat shock transformation. Transformation cultures are plated on Luria Broth (LB) containing 100 μg/ml ampicillin and after overnight growth a single ampicillin-resistant colony is used to inoculate 5 ml of LB containing 100 μg/ml ampicillin. After growth for 10–16 hours with shaking (225 rpm) at 37° C., this culture is used to inoculate 1 L of M9 minimal medium (M9 salts, 2% glucose, 0.01 mg/mL thiamine, 100 μg/ml ampicillin, supplemented with all amino acids at 20 μg/mL except proline which is supplemented at 12.5 mg/L) in a 1.5 L shaker flask. After growth at 37° C., 225 rpm, for 15–20 hours post-inoculation, the optical density at 600 nm is constant at approximately 0.5 OD/ml. The cells are harvested by centrifugation (5000 rpm, 5 minutes), the media decanted, and the cells resuspended in 1 L of M9 minimal media containing 100 μg/ml ampicillin, 0.08M L-hydroxyproline, and 0.5M NaCl. Following growth for 1 hour at 37° C., 225 rpm, IPTG is added to 1 mM and the cultures allowed to grow for an additional 5–15 hours. Cells are harvested by centrifugation (5000 rpm, 10 minutes) and lysed by mechanical disruption. The hydroxyproline-containing collagen fragment is purified by ammonium sulfate fractionation and column chromatography.

It will be understood that various modifications may be made to the embodiments disclosed herein. For example, it is contemplated that any protein produced by prokaryotes and eukaryotes can be made to incorporate one or more amino acid analogs in accordance with the present disclosure. Therefore, the above description should not be construed as limiting, but merely as exemplifications of preferred embodiments. Those skilled in art will envision other modifications within the scope and spirit of the claims appended hereto.

---

What is claimed is:

1. A method of incorporating an amino acid analog into at least one polypeptide produced by a cell selected from the group consisting of prokaryotic cell and eukaryotic cell comprising:

providing a cell selected from the group consisting of a prokaryotic cell and eukaryotic cell;

providing hypertonic growth media containing at least one amino acid analog selected from the group consisting of trans-4-hydroxyproline and 3-hydroxyproline; and contacting the cell with the growth media wherein the at least one amino acid analog is assimilated into the cell and incorporated into at least one polypeptide.

2. A method according to claim 1 wherein the cell is a proline auxotroph.

3. A method according to claim 2 wherein the cell is selected from the group consisting of bacterial cell, yeast cell and insect cell.

4. A method according to claim 1 wherein the at least one polypeptide is at least a portion of a collagen molecule.

5. A method according to claim 4 wherein the polypeptide is encoded for by the nucleic acid sequence shown in Seq. ID No. 1.

6. A method according to claim 4 wherein the polypeptide is a fragment encoded for by the nucleic acid sequence shown in Seq. ID No. 2.

7. A method according to claim 4 wherein the polypeptide is encoded for by the nucleic acid sequence shown in Seq. ID No. 3.

8. A method according to claim 4 wherein the at least a portion of a collagen is fused to a physiologically active substance.

9. A method according to claim 8 wherein the physiologically active substance is a bone morphogenic protein.

10. A method according to claim 1 wherein nucleic acid encoding the at least one polypeptide is carried on a replicable expression vector.

11. A method according to claim 10 wherein the replicable expression vector is a plasmid.

12. A method according to claim 3 wherein the proline auxotroph is selected from the group consisting of *E. coli* and *S. cerevisiae*.

13. A method according to claim 1 wherein the at least one polypeptide is at least a portion of a maltose binding protein molecule.

14. A method according to claim 1 wherein an osmolality increasing agent selected from a group consisting of NaCl, KCl, $MgCl_2$, sucrose, glucose, maltose, PEG, dextran, cellulose and glycine is added to the growth media.

15. A method according to claim 14 wherein NaCl ranges from about 0.5M to about 1M.

16. A method according to claim 1 wherein the growth media contains an amount of proline which causes proline starvation of the cell.

17. A method of substituting an amino acid analog in a polypeptide manufactured by a cell selected from the group consisting of prokaryotic cell and eukaryotic cell comprising:

providing a cell selected from the group consisting of prokaryotic cell and eukaryotic cell;

providing hypertonic growth media containing at least one amino acid analog selected from the group consisting of trans-4-hydroxyproline and 3-hydroxyproline ; and contacting the cell with the growth media wherein the at least one amino acid analog is assimilated into the cell and incorporated as a substitution for at least one naturally occurring amino acid in at least one polypeptide.

18. A method of controlling the amount of an amino acid analog incorporated into a polypeptide comprising:

providing a first cell selected from the group consisting of prokaryotic cell and eukaryotic cell:

providing a first hypertonic growth media containing a first predetermined amount of at least one amino acid analog selected from the group consisting of trans-4-hydroxyproline and 3-hydroxyproline; and contacting the cell with the first growth media wherein a first amount of amino acid analog is assimilated into the first cell and incorporated into at least one polypeptide;

providing at least a second cell selected from the group consisting of prokaryotic cell and eukaryotic cell;

providing a second hypertonic growth media containing a second predetermined amount of at least one amino acid analog selected from the group consisting of trans-4-hydroxyproline and 3-hydroxyproline ; and contacting the at least second cell with the second growth media wherein a second amount of amino acid analog is assimilated into the second cell and incorporated into at least one polypeptide.

19. A method of increasing stability of a recombinant polypeptide produced by a cell comprising:

providing a cell selected from the group consisting of prokaryotic cell and eukaryotic cell;

providing hypertonic growth media containing an amino acid analog selected from the group consisting of trans-4-hydroxyproline, 3-hydroxyproline and combinations thereof; and contacting the cell with the growth media wherein the amino acid analog is assimilated into the cell and incorporated into a recombinant polypeptide, thereby stabilizing the polypeptide.

20. A method of increasing uptake of an amino acid analog into a cell and causing formation of an amino acid analog/tRNA complex comprising:

providing a cell selected from the group consisting of prokaryotic cell and eukaryotic cell;

providing hypertonic growth media containing an amino acid analog selected from the group consisting of trans-4-hydroxyproline, 3-hydroxyproline and combinations thereof; and contacting the cell with the hypertonic growth media wherein the amino acid analog is assimilated into the cell and incorporated into an amino acid analog/tRNA complex.

21. A composition comprising a cell selected from group consisting of prokaryotic cell and eukaryotic cell and hypertonic growth media including at least one amino acid analog selected from the group consisting of trans-4-hydroxyproline and 3-hydroxyproline wherein the hypertonic growth media increases cell uptake of the at least one amino acid analog.

* * * * *